United States Patent [19]

Hayes, Jr. et al.

[11] Patent Number: 4,826,603

[45] Date of Patent: May 2, 1989

[54] HYDROCARBON GROUP-TYPE ANALYZER SYSTEM

[75] Inventors: Paul C. Hayes, Jr., Kettering; Steven D. Anderson, Dayton, both of Ohio

[73] Assignee: United States of America as represented by the Secretary of the Air Force, Washington, D.C.

[21] Appl. No.: 243,537

[22] Filed: Sep. 12, 1988

Related U.S. Application Data

[62] Division of Ser. No. 160,746, Feb. 12, 1988, which is a division of Ser. No. 905,413, Sep. 9, 1986, abandoned.

[51] Int. Cl.⁴ .......................................... G01D 15/08
[52] U.S. Cl. .................................... 210/635; 210/659; 73/61.1 C; 422/70; 436/161
[58] Field of Search ............ 210/635, 656, 659, 198.2, 210/502.1; 55/67, 386; 73/61.1 C; 422/70; 436/161

[56] References Cited

U.S. PATENT DOCUMENTS

| | | | |
|---|---|---|---|
| 3,298,160 | 1/1967 | Hoffman | 55/67 |
| 3,940,972 | 3/1976 | Norell | 55/67 |
| 3,966,596 | 6/1976 | Stevens | 210/198.2 |
| 3,987,058 | 10/1976 | Saunders | 210/198.2 |
| 4,003,243 | 1/1977 | Blu | 73/61.1 C |
| 4,254,656 | 3/1981 | Sanford | 210/198.2 |
| 4,341,634 | 7/1982 | Matsushita | 210/656 |
| 4,366,060 | 12/1982 | Leiser | 210/198.2 |
| 4,446,105 | 5/1984 | Dinsmore | 210/198.2 |
| 4,671,103 | 6/1987 | Dickakian | 73/61.1 C |

Primary Examiner—Ernest G. Therkorn
Attorney, Agent, or Firm—Charles E. Bricker; Donald J. Singer

[57] ABSTRACT

This invention concerns analysis by high performance liquid chromatography (HPLC) of crude oils and petroleum products.

In one embodiment of the invention a sample is quantitatively separated into saturates, alkyl benzenes and polynuclear aromatics using a system comprising a column packed with a porous silica packing material having a polar amino-cyano bonded phase in tandem with a column packed with a tetranitrofluorenimino packing material, and a dielectric constant detector.

In another embodiment of the invention a sample is qualitatively separated into saturates, olefins, and total aromatics using a system employing an olefin-selective column and a dielectric constant detector.

2 Claims, 1 Drawing Sheet

HYDROCARBON GROUP-TYPE ANALYZER SYSTEM

RIGHTS OF THE GOVERNMENT

The invention described herein may be manufactured and used by or for the Government of the United States for all governmental purposes withut the payment of any royalty.

This is a division of allowed application Ser. No. 160,746, filed Feb. 12, 1988, which in turn is a division of application Ser. No. 905,413, filed Sept. 9, 1986, now abandoned.

BACKGROUND OF THE INVENTION

This invention relates to chromatography. In one aspect this invention relates to the high performance liquid chromatographic separation of a liquid hydrocarbon mixture into three components, namely saturates, alkyl benzenes and polynuclear aromatics. In another aspect this invention relates to the high performance liquid chromatographic separation of a liquid hydrocarbon mixture into three components, namely saturates, olefins, and total aromatics.

The abundance of high quality, low cost petroleum crudes and feedstocks is rapidly diminishing. Current feedstocks incorporate lower grade crudes and off-streams as well as processed liquids from alternate sources of energy, such as shale oil, tar sands, coal liquids, and biomass materials. The petrochemical engineer needs timely and accurate analytical results in order to optimize refinery operations and monitor product character.

Liquid chromatography has been employed to characterize the group composition of crude oils and petroleum products since the beginning of this century. The fluorescent indicator adsorption (FIA) method, ASTM D 1319, has served for over 30 years as the official method of the petroleum industry for measuring the paraffinic, olefinic, and aromatic content of gasolines and jet fuels.

High performance liquid chromatography (HPLC) offers many advantages over open column chromatography, not the least of which is speed. However, a severe shortcoming of most HPLC approaches to a hydrocarbon group-type analysis is the difficulty in obtaining accurate response factors applicable to different distillate products. Accuracy is generally compromised when these response factors are used to analyze hydrotreated and hydrocracked materials. Given significant changes in the hydrocarbon distribution within a certain group-type, analytical results will be misleading for such samples because of the variation in response exhibited by most routinely used HPLC detectors.

It is an object of the present invention to provide an analytical method whereby the saturates, alkyl benzenes, and polynuclear aromatics in a solution consisting of many kinds of hydrocarbon compounds can be easily and quickly analyzed with high reproducibility and accuracy.

It is another object of this invention to provide an apparatus for performing the above method.

It is a further object of the present invention to provide an analytical method whereby the saturates, olefins, and total aromatics in a solution consisting of many kinds of hydrocarbon compounds can be easily and quickly analyzed with high reproducibility and accuracy.

It is yet a further object of this invention to provide an apparatus for performing the above method.

Other objects and advantages of the present invention will be apparent to those skilled in the art.

SUMMARY OF THE INVENTION

In accordance with one aspect of the present invention there is provided a method of analysis by high performance liquid chromatography for obtaining an analysis of three components, namely saturates, alkyl benzenes and polynuclear aromatics, present in a liquid hydrocarbon mixture which comprises the steps of:

(a) introducing a sample of the mixture to be analyzed into a first column, which column is packed with a porous silica type packing material having a polar amino-cyano bonded phase;

(b) thereafter introducing into the first column as the eluent on organic chlorine-containing solvent;

(c) passing the stream from the first column into a second column packed with a tetranitrofluorenimino packing material; and (d) passing the eluate from the second column into a dielectric constant detector to detect the eluate quantitatively for saturates, alkyl benzenes, and polynuclear aromatics.

In accordance with another aspect of the present invention there is provided a method of analysis by high performance liquid chromatography for obtaining an analysis of three components, namely saturates, olefins, and total aromatics, present in a liquid hydrocarbon mixture which comprises the steps of:

(a) introducing a sample of the mixture to be analyzed into an olefin-selective column;

(b) thereafter introducing into the column an eluent;

(c) passing the stream from the column into a dielectric constant detector to detect the eluate quantitatively for saturates and total aromatics;

(d) backflushing the column; and (e) passing the stream from the column into the detector to detect the eluate quantitatively for olefins.

Also provided in accordance with this aspect of the invention is an improved olefin-selective column, described hereinafter.

DESCRIPTION OF THE PREFERRED EMBODIMENTS

Figure 1:
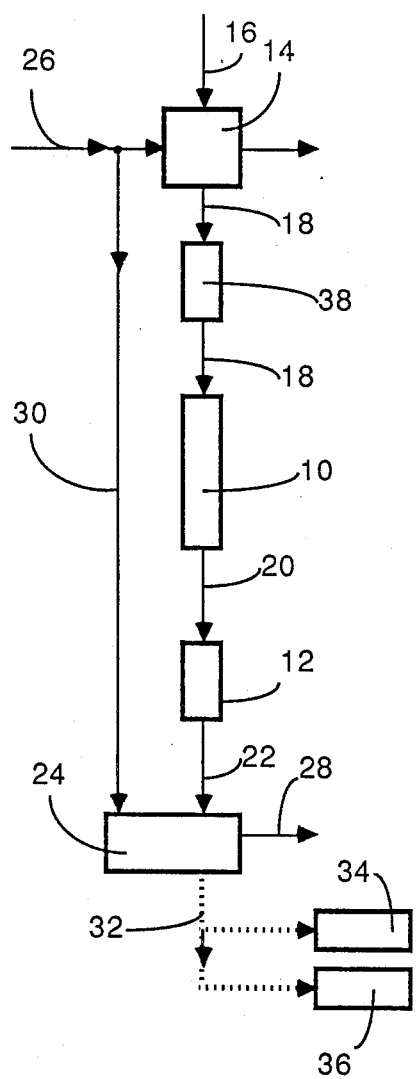
FIG. 1 is a representation of a first chromatographic analyzer system of the present invention.

Referring to FIG. 1, there is shown a first chromatographic column 10 and a second chromatographic column 12. A sample of a fluid to be analyzed is delivered to sample valve 14 through conduit means 16. A conduit means 18 extends between sample valve 14 and the inlet to column 10. Columns 10 and 12 are connected by conduit means 20. A conduit means 22 extends between the outlet of column 12 and the sample inlet of a dielectric constant detector 24. The carrier fluid is delivered to sample valve 14 through conduit means 26. The effluent from the detector 24 is vented through conduit means 28. Carrier fluid is passed to the reference portion of detector 24 through conduit means 30.

At the beginning of an analysis period, sample valve 14 is actuated to introduce a predetermined volume of sample into the carrier fluid flowing through the columns 10 and 12. The amount of the sample to be introduced can be selected as desired; however, generally 0.5 to 200 microliters is sufficient for the analysis. The constituents of the sample are eluted in sequence from the column 10 via conduit means 20 into column 12 thence from column 12 via conduit means 22 to the sample side of dielectric constant detector 24. Detector 24 provides an output signal 32 in response to a constituent in the sample. Output signal 32 may be passed to one or both of strip chart recorder 34 or integrator 36. Optionally, a guard column 38 may be interposed in conduit means 18 between valve 14 and column 10.

The method of the first aspect of the present invention may be employed for the quantitative analysis of various fuels, crude oils, synthetic fuels, and residual fuels. This method provides a hydrocarbon group-type analysis with an accuracy not affected by the carbon-number distribution of the sample. Generally these fuels and oils contain varying amounts of $C_6$ to $C_{16}$ hydrocarbons including cyclic and acyclic saturates, alkyl benzenes, polynuclear aromatics, and olefins. The best results have been obtained for a first group containing nonaromatic hydrocarbons including alkanes, cycloalkanes, and alkenes, a second group containing alkyl benzenes, and a third group containing polynuclear aromatic hydrocarbons. Exemplary nonaromatics include normal and branched hydrocarbons such as hexane, nonane, dodecane, pentadecane, iso-octane, 2,2,3-trimethylbutane, 2,2,5-trimethylhexane, hendecane, cyclohexane, methylcyclohexane, decalins, and the like. Exemplary alkenes or olefins include 2-heptenes, 1-octene, 1-decene, 3,5,5-trimethyl-1-hexene, 1-tridecene, 1-hexadecene, and the like. Exemplary alkyl benzenes include toluene, xylenes, isopropylbenzene, tetralin, cyclohexylbenzene, phenyloctane and the like. Exemplary polynuclear aromatic hydrocarbons include naphthalene, 2-methylnaphthalene, 2,6-dimethylnaphthalene, biphenyl, bibenzyl, anthracene, and the like.

Any suitable, substantially non-polar eluent or carrier fluid may be utilized. In general, eluents will have a low viscosity, a relatively low solvent strength to enable the chromatographic columns to resolve hydrocarbon groups that characteristically display low capacity factors, and a relatively high dielectric constant to provide uniformity of response in the detector. Suitable eluents include halogen-containing materials such as methylene chloride, 1,1-dichloroethane, n-butyl chloride, and the like, with n-butyl chloride being particularly preferred.

Referring again to FIG. 1, first column 10 is packed with a silica type packing material having a polar amino-cyano bonded phase. A commercially available column is the Partisil PAC column, available from Whatman, Inc., Clifton, NJ, which has a silica gel stationary phase and a bonded phase consisting of alkyl groups containing amino-cyano groups in a 2:1 ratio.

Second column 12 which is packed with a tetranitrofluorenimino packing material is commercially available from ES Industries, Marlton, N.J.

A commercially dielectric constant detector is the Optichrom Model 430, manufactured by Applied Automation, Inc., Bartlesville, OK.

The processing of the output signal 32 may be accomplished in a variety of ways, including those described previously. Those skilled in the art will be aware of other signal processing methods.

The detector may be calibrated using a mixture of hydrocarbons of known composition. For example, iso-octane may represent the saturates, including the alkenes, ethyl benzene may represent the alkyl benzenes and 3,3-dimethyldiphenyl may represent the polynuclear aromatics.

Figure 2:
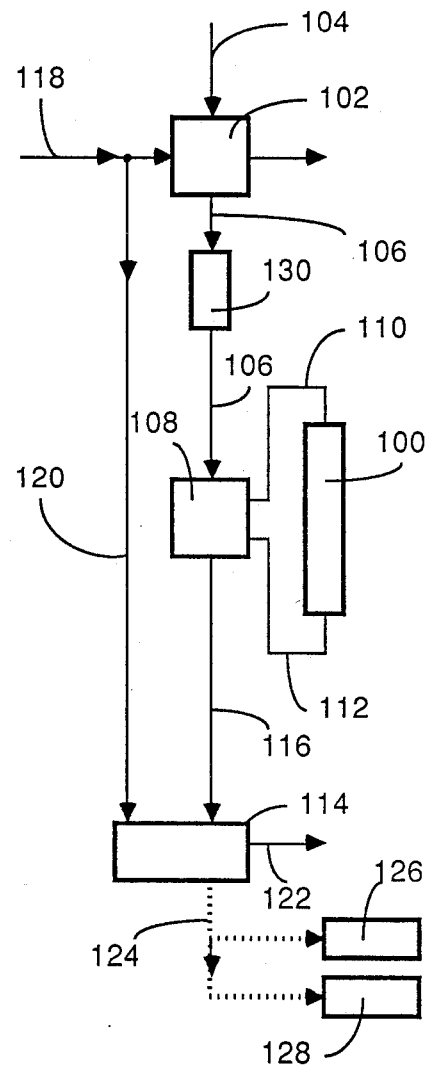
FIG. 2 is a representation of another chromatographic analyzer system of this invention.

Referring now to FIG. 2, there is shown a chromatographic column 100, a sample of the fluid to be analyzed is delivered to sample valve 102 through conduit means 104. A conduit means 106 extends between sample valve 102 and backflush valve 108. The ends of column 100 are connected to backflush valve 108 by conduit means 110 and 112, and backflush valve 108 is connected to the dielectric constant detector 114 by conduit means 116. The carrier fluid is delivered to sample valve 102 through conduit means 118, and to the reference portion of detector 114 through conduit means 120. The effluent from detector 114 is vented through conduit means 122. Detector 114 provides an output signal 124 in response to a constituent in the sample. This signal may be passed to one or both of strip chart recorder 126 or integrator 128. Optionally, a guard column 130 may be interposed in conduit means 106 between valve 102 and valve 108.

The method of the seciond aspect of the present invention may also be employed for the quantitative analysis of various fuels, crude oils, synthetic fuels, and residual fuels. This method provides a hydrocarbon group-type analysis with an accuracy not affected by the carbon-number distribution of the sample. Generally these fuels and oils contain varying amounts of $C_6$ to $C_{16}$ hydrocarbons including cyclic and acyclic saturates, alkyl benzenes, polynuclear aromatics, and olefins. The best results have been obtained for a first group containing nonaromatic hydrocarbons, including alkanes and cycloalkanes, a second group containing aromatics including alkyl aromatics, and a third group containing internal and terminal mono-olefins, conjugated and uncionjugated di-olefins, cyclo-olefins and aromatic cyclo-olefins. Exemplary nonaromatics include normal and branched hydrocarbons such as hexane, nonane, dodecane, pentadecane iso-octane, 2,2,3-trimethylbutane, 2,2,5-trimethylhexane, hendecane, cyclohexane, methylcyclohexane, decalins, and the like. Exemplary olefins include 2-heptenes, 1-octene, 1-decene, 3,5,5-trimethyl-1-hexene, 1-tridecene, 1-hexadecene, and the like. Exemplary aromatic hydrocarbons include toluene, xylenes, isopropylbenzene, tetralin, cyclohexylbenzene, phenyloctane, naphthalene, 2-methylnaphthalene, 2,6-dimethyl naphthalene, biphenyl, bibenzyl, anthracene, and the like.

Column 100 is an olefin-selective column. This column is prepared by treating a column having a suitable support and a cation exchange resin bonded phase with silver. A suitable commercially available column is the Partisil SCX column, available from Whatman, Inc., Clifton, NJ. This column has a silica gel stationary phase and a bonded phase comprising aromatic benzene sulfonic acid functional groups. For use in the present invention, the column is first flushed with distilled water. Next, an aqueous solution of silver nitrate is pumped through the column. The column is then flushed with distilled water until no silver nitrate is detected in the effluent, i.e., generally about 100 ppm silver ion or less. Finally, a suitable water absorber, such as dry methanol, dry acetonitride, dry acetone, or the like, is pumped through the treated column to remove water.

At the beginning of an analysis period, sample valve 102 is actuated to introduce a predetermined volume of sample into the carrier fluid flowing through column 100. Initially, the back-flush valve 108 is positioned so that material flow is from conduit means 106, through valve 108, through conduit means 110, through conduit means 112, through valve 108, through conduit means 116 to detector 114. The amount of the sample to be introduced can be selected as desired; however, generally 0.5 to 200 microliters is sufficient for the analysis. After the saturates and aromatics elute from the column, valve 108 is repositioned so that material flow is from conduit means 106, through valve 108, through conduit means 112, through column 100, through conduit means 110, through valve 108, through conduit means 116 to detector 114, whereby the olefins on column 100 are eluted to the detector 114.

Any suitable, substantially non-polar eluent or carrier fluid may be utilized. In general, eluents will have a low viscosity, a relatively low solvent strength to enable the chromatographic columns to resolve hydrocarbon groups that characteristically display low capacity factors, and a relatively high dielectric constant to provide uniformity of response in the detector. Suitable eluents include halogen-containing materials such as methylene chloride, 1,1-dichloroethane, n-butyl chloride, and the like, as well as mixed-halogen-containing materials, such as dichlorofluoromethane, chlorodifluoromethane, 2,2-dichloro-1,1,1-trifluoroethane and the like, with 2,2-dichloro-1,1,1-trifluoroethane being preferred.

In the examples which follow, determinations were made using a Varian Model 4200 Liquid Chromatograph (Varian Associates, Walnut Creek, Calif.) equipped with a Varian Model 8000 autosampler, a six-port injection valve with a 10 microliter sample loop, and an Optichrom Model 430 Dielectric Constant Detector, operated at a backpressure of about 1000 psig. A guard column packed with 30–40 micron pellicular silica preceded the analytical columns. uantitation was accomplished using a Hewlett Packard Model 3357 Laboratory Automation System. The HPLC results are compared to FIA (ASTM D1319) and mass spectrometric (ASTM D2789) methods. The quantitative results were determined directly in volume percent for each method.

In Examples, I–VII, the analytical columns consisted of two Partisil PAC columns, 250×4.6 mm i.d., 5 micron particle size, in tandem, followed by one TENF (tetranitrofluorenimino) column, 300×4.6 mm i.d., 10 micron particle size. HPLC grade n-butyl chloride, previously dried over molecular sieves, was used for the mobile phase. The detector was calibrated with a mixture of 1 ml each of iso-octane, ethyl benzene, and 3,3-dimethyldiphenyl diluted to 100 ml with n-butyl chloride. Response factors of 1.00 for the saturates, 1.10 for the alkyl benzenes and 1.20 for the polynuclear aromatics were obtained.

EXAMPLE I

| Composition of Sample Mixture 1 | | | |
|---|---|---|---|
| Hydrocarbon Class | Carbon No. | Component Name | Volume Percent |
| Saturates | — | — | 87.5 |
|  | 6 | Cyclohexane | 25.0 |
|  | 7 | Methylcyclohexane | 25.0 |
|  | 12 | Dodecane | 12.5 |
|  | 16 | Hexadecane | 25.0 |
| Alkyl Benzenes | — | — | 12.5 |
|  | 12 | Cyclohexylbenzene | 12.5 |

| Analysis of Sample Mixture 1 | | | | |
|---|---|---|---|---|
|  | HPLC | FIA | MS | Known |
| Saturates | 87.7 | 87.0 | 84.2 | 87.5 |
| Olefins | — | 0.7 | — | 0.0 |
| Alkyl Benzenes | 12.3 | — | 15.8 | 12.5 |
| Polynuclear Arom. | 0.0 | — | 0.0 | 0.0 |
| Total Arom. | 12.3 | 12.3 | 15.8 | 12.5 |

EXAMPLE II

| Composition of Sample Mixture 2 | | | |
|---|---|---|---|
| Hydrocarbon Class | Carbon No. | Component Name | Volume Percent |
| Saturates | — | — | 71.4 |
|  | 7 | Methlcyclohexane | 14.3 |
|  | 8 | Iso-octane | 28.5 |
|  | 10 | Decane | 14.3 |
|  | 12 | Dodecane | 14.3 |
| Alkyl Benzenes | — | — | 28.6 |
|  | 7 | Toluene | 14.3 |
|  | 8 | p-Xylene | 14.3 |

| Analysis of Sample Mixture 2 | | | | |
|---|---|---|---|---|
|  | HPLC | FIA | MS | Known |
| Saturates | 72.4 | 71.3 | 73.8 | 71.4 |
| Olefins | — | 0.7 | — | 0.0 |
| Alkyl Benzenes | 27.6 | — | 26.2 | 28.6 |
| Polynuclear Arom. | 0.0 | — | 0.0 | 0.0 |
| Total Arom. | 27.6 | 28.0 | 26.2 | 28.6 |

EXAMPLE III

| Composition of Sample Mixture 3 | | | |
|---|---|---|---|
| Hydrocarbon Class | Carbon No. | Component Name | Volume Percent |
| Saturates | — | — | 53.5 |
|  | 7 | Methylcyclohexane | 3.9 |
|  | 7 | 2-Methylhexane | 2.2 |
|  | 7 | 2,2,3-Trimethylbutane | 6.5 |
|  | 8 | Iso-octane | 5.2 |
|  | 9 | Nonane | 5.2 |
|  | 9 | 4-Methyloctane | 1.2 |
|  | 9 | 2,5-Dimethylheptane | 0.8 |
|  | 9 | 2,2,5-Trimethylhexane | 3.9 |
|  | 10 | Decane | 5.2 |
|  | 11 | Hendacane | 5.2 |
|  | 11 | 2-Methyldecane | 1.2 |
|  | 12 | Dodecane | 5.2 |
|  | 15 | Pentadecane | 3.9 |
|  | 16 | Hexadecane | 3.9 |
| Alkyl Benzenes | — | — | 46.5 |
|  | 7 | Toluene | 5.2 |
|  | 8 | m-Xylene | 5.2 |
|  | 8 | p-xylene | 6.5 |
|  | 9 | 1,3,5-Trimethylbenzene | 3.8 |
|  | 9 | 1-Ethyl-4-Methylbenzene | 5.2 |
|  | 9 | Isopropylbenzene | 3.8 |
|  | 10 | Tetrahydronaphthalene | 2.5 |
|  | 12 | Cyclohexylbenzene | 7.8 |
|  | 14 | Phenyloctane | 6.5 |

| Analysis of Sample Mixture 3 | | | | |
|---|---|---|---|---|
|  | HPLC | FIA | MS | Known |
| Saturates | 53.5 | 52.0 | 56.1 | 53.5 |
| Olefins | — | 0.0 | — | 0.0 |
| Alkyl Benzenes | 46.5 | — | 43.9 | 46.5 |
| Polynuclear Arom. | 0.0 | — | 0.0 | 0.0 |
| Total Arom. | 46.5 | 47.2 | 43.9 | 46.5 |

EXAMPLE IV

Composition of Sample Mixture 4

| Hydrocarbon Class | Carbon No. | Component Name | Volume Percent |
|---|---|---|---|
| Saturates | — | — | 71.4 |
| | 6 | Cyclohexane | 9.2 |
| | 7 | 2-Methylhexane | 1.6 |
| | 7 | 3-Methylhexane | 2.0 |
| | 7 | Methylcyclohexane | 7.0 |
| | 8 | Octane | 2.9 |
| | 8 | Iso-octane | 4.0 |
| | 9 | Nonane | 4.7 |
| | 9 | 3-Methyloctane | 1.2 |
| | 9 | 2,5-Dimethylheptane | 2.4 |
| | 10 | Decane | 4.7 |
| | 10 | 3,6-Dimethyloctane | 1.6 |
| | 10 | 4-Propylheptane | 0.8 |
| | 10 | Decalins (c,t) | 1.8 |
| | 10 | JP-10 | 10.6 |
| | 11 | Hendecane | 1.9 |
| | 11 | 2-Methyldecane | 0.7 |
| | 12 | Dodecane | 9.5 |
| | 15 | Pentadecane | 1.9 |
| | 16 | Hexadecane | 2.9 |
| Alkyl Benzenes | — | — | 16.8 |
| | 7 | Toluene | 6.5 |
| | 8 | m-Xylene | 10.3 |
| Polynuclear Arom. | — | — | 11.8 |
| | 10 | Naphthalene | 2.3 |
| | 11 | 2-Methylnaphthalene | 3.4 |
| | 12 | 2-Ethylnaphthalene | 1.6 |
| | 12 | 2,3-Dimethylnaphthalene | 1.2 |
| | 12 | 2,6-Dimethylnaphthalene | 0.6 |
| | 12 | Biphenyl | 1.6 |
| | 14 | Bibenzyl | 1.1 |

Analysis of Sample Mixture 4

| | HPLC | FIA | MS | Known |
|---|---|---|---|---|
| Saturates | 71.4 | 70.0 | 67.0 | 71.4 |
| Olefins | — | 0.0 | — | 0.0 |
| Alkyl Benzenes | 16.8 | — | 20.0 | 16.8 |
| Polynuclear Arom. | 11.8 | — | 12.2 | 11.8 |
| Total Arom. | 28.6 | 29.2 | 32.2 | 28.6 |

EXAMPLE V

Composition of Sample Mixture 5

| Hydrocarbon Class | Carbon No. | Component Name | Volume Percent |
|---|---|---|---|
| Saturates | — | — | 51.1 |
| | 6 | Cyclohexane | 7.3 |
| | 7 | 2-Methylhexane | 2.6 |
| | 7 | 3-Methylhexane | 3.3 |
| | 7 | Methylcyclohexane | 5.5 |
| | 8 | Octane | 0.2 |
| | 8 | Iso-octane | 6.6 |
| | 9 | Nonane | 0.4 |
| | 9 | 3-Methyloctane | 2.1 |
| | 9 | 2,5-Dimethylheptane | 4.2 |
| | 10 | Decane | 0.4 |
| | 10 | 3,6-Dimethyloctane | 2.9 |
| | 10 | 4-Propylheptane | 1.4 |
| | 10 | Decalins (c,t) | 1.6 |
| | 10 | JP-10 | 10.1 |
| | 11 | Hendecane | 0.1 |
| | 11 | 2-Methyldecane | 1.3 |
| | 12 | Dodecane | 0.6 |
| | 15 | Pentadecane | 0.2 |
| | 16 | Hexadecane | 0.2 |
| Alkyl Benzenes | — | — | 38.9 |
| | 7 | Toluene | 7.3 |
| | 8 | m-Xylene | 10.5 |
| | 8 | p-Xylene | 2.8 |
| | 9 | Isopropylbenzene | 1.4 |
| | 9 | 1,2,4-Trimethylbenzene | 2.8 |
| | 9 | 1,3,4-Trimethylbenzene | 1.7 |
| | 10 | Butylbenzene | 1.1 |
| | 10 | Tetralin | 1.6 |
| | 12 | 2-Methylpentylbenzene | 0.8 |
| | 12 | Cyclohexylbenzene | 6.1 |
| | 14 | Phenyloctane | 2.8 |
| Polynuclear Arom. | — | — | 10.0 |
| | 10 | Naphthalene | 2.0 |
| | 11 | 2-Methylnaphthalene | 2.8 |
| | 12 | 2-Ethylnaphthalene | 1.4 |
| | 12 | 2,3-Dimethylnaphthalene | 1.0 |
| | 12 | 2,6-Dimethylnaphthalene | 0.5 |
| | 12 | Biphenyl | 1.4 |
| | 14 | Bibenzyl | 0.9 |

Analysis of Sample Mixture 5

| | HPLC | FIA | MS | Known |
|---|---|---|---|---|
| Saturates | 53.1 | 48.0 | 46.9 | 51.1 |
| Olefins | — | 1.5 | — | 0.0 |
| Alkyl Benzenes | 36.7 | — | 42.2 | 38.9 |
| Polynuclear Arom. | 10.2 | — | 10.9 | 10.0 |
| Total Arom. | 46.9 | 50.5 | 53.1 | 48.9 |

EXAMPLE VI

Composition of Sample Mixture 6

| HC Group-Type | Blending Stock/Pure Component | Volume Percent |
|---|---|---|
| Saturates | — | 70.0 |
| | hydrocracked n-C16 (C6–C16 isomers) | 40.0 |
| | methylcyclohexane | 10.0 |
| | JP-10 (Dicycloparaffin) | 20.0 |
| Alkyl Benzenes | — | 20.0 |
| | xylene bottoms blending stock | 19.0 |
| | toluene | 1.0 |
| Polynuclear Aron. | — | 5.0 |
| | 2-Methylnaphthalene | 3.0 |
| | 1-Ethylnaphthalene | 1.0 |
| | 1,4-Dimethylnaphthalene | 1.0 |
| Olefins | — | 5.0 |
| | 2-Heptenes (c,t) | 2.0 |
| | 1-Octene | 2.0 |
| | 1-Decene | 1.0 |

Analysis of Sample Mixture 6

| | HPLC | FIA | MS | Known |
|---|---|---|---|---|
| Saturates | 74.9 | 68.8 | 69.3 | 70.0 |
| Olefins | — | 3.7 | — | 5.0 |
| Alkyl Benzenes | 20.1 | — | 24.8 | 20.0 |
| Polynuclear Arom. | 5.0 | — | 5.8 | 5.0 |
| Total Arom. | 25.1 | 27.5 | 30.7 | 25.0 |

Examination of the analyses given in Examples I–VI reveals that the method of the present invention compares very favorably with the ASTM methods.

EXAMPLE VII

Analyses of several fuels are given in the following tables:

| | HPLC | FIA | MS |
|---|---|---|---|
| Comparative Analysis of Petroleum-derived JP-4 | | | |
| Saturates | 89.0 | 86.2 | 90.0 |
| Olefins | — | 1.5 | — |
| Alkyl Benzenes | 10.3 | — | 9.5 |
| Polynuclear Arom. | 0.7 | — | 0.5 |
| Total Arom. | 11.0 | 12.3 | 10.0 |
| Comparative Analysis of Shale-derived JP-4 | | | |
| Saturates | 87.6 | 86.8 | 89.9 |
| Olefins | — | 1.5 | — |
| Alkyl Benzenes | 12.3 | — | 10.1 |
| Polynuclear Arom. | 0.1 | — | 0.0 |
| Total Arom. | 12.4 | 11.7 | 10.1 |
| Comparative Analysis of Shale-derived JP-8 | | | |

|  | HPLC | FIA | MS |
|---|---|---|---|
| Saturates | 80.7 | 76.2 | 79.5 |
| Olefins | — | 1.6 | — |
| Alkyl Benzenes | 18.9 | — | 19.7 |
| Polynuclear Arom. | 0.4 | — | 0.8 |
| Total Arom. | 19.3 | 22.2 | 20.5 |
| Comparative Analysis of Petroleum-derived Diesel Fuel No. 2 | | | |
| Saturates | 76.4 | 65.0 | 78.4 |
| Olefins | — | 2.9 | — |
| Alkyl Benzenes | 14.3 | — | 14.1 |
| Polynuclear Arom. | 9.3 | — | 7.5 |
| Total Arom. | 23.6 | 32.1 | 21.6 |

In Examples VIII–XIII, the analytical column consisted of a silver nitrate-modified Partisil SCX column, 100×4.6 mm i.D., 5 μm particle size, prepared as described previously by passing about 50 ml of 1M silver nitrate through a fresh column, flushing with distilled water, and finally, flushing with acetone to remove residual water. Freon 123 (2,2-dichloro-1,1,1-trifluoroethane), available from Halocarbon Products Corp., Hackensack, N.J., was used for the mobile phase. Response factors of unity were used.

EXAMPLE VIII

| Composition of Sample Mixture 7 | | |
|---|---|---|
| HC Group-Type | Blending Stock/Pure Component | Volume Percent |
| Saturates | — | 40.0 |
|  | hydrocracked n-C16 (C6–C16 isomers) | 10.0 |
|  | "isopar C" (Exxon isoparaffinic solvent, b.p.= 98–106 deg C.) | 20.0 |
|  | "Exxsol D80" (Exxon aliphatic, high naphthenic solvent, b.p.= 202–232 deg C.) | 10.0 |
| Alkyl Benzenes | — | 55.0 |
|  | toluene | 2.0 |
|  | tetralin | 10.0 |
|  | 1-t-butyl-4-ethylbenzene | 2.0 |
|  | n-octylbenzene | 1.0 |
|  | xylene bottoms (C8–C10 benzenes) | 40.0 |
| Alkyl Naphthalenes | — | 5.0 |
|  | 2-Methylnaphthalene | 3.0 |
|  | 1,2-dimethylnaphthalene | 2.0 |
| Olefins | — | 0.0 |

| Analysis of Sample Mixture 7 | | | |
|---|---|---|---|
|  | HPLC | FIA | Known |
| Saturates | 40.2 | 39.2 | 40.0 |
| Olefins | 0.0 | 1.0 | 0.0 |
| Total Arom. | 59.8 | 59.8 | 60.0 |

EXAMPLE IX

| Composition of Sample Mixture 8 | | |
|---|---|---|
| HC Group-Type | Blending Stock/Pure Component | Volume Percent |
| Saturates | — | 70.0 |
|  | hydrocracked n-C16 (C6–C16 isomers) | 40.0 |
|  | methylcyclohexane | 10.0 |
|  | JP-10 (dicycloparaffin) | 20.0 |
| Alkyl Benzenes | — | 20.0 |
|  | xylene bottoms (C8–C10 benzenes) | 19.0 |
|  | toluene | 1.0 |
| Alkyl Naphthalenes | — | 5.0 |
|  | 2-Methylnaphthalene | 3.0 |
|  | 1-ethylnaphthalene | 1.0 |
|  | 1,4-dimethylnaphthalene | 1.0 |
| Olefins | — | 5.0 |
|  | 2-heptenes (c,t) | 2.0 |
|  | 1-octene | 2.0 |
|  | 1-decene | 1.0 |

| Analysis of Sample Mixture 8 | | | |
|---|---|---|---|
|  | HPLC | FIA | Known |
| Saturates | 69.0 | 65.4 | 70.0 |
| Olefins | 5.0 | 6.6 | 5.0 |
| Total Arom. | 26.0 | 28.0 | 25.0 |

EXAMPLE X

| Composition of Sample Mixture 9 | | |
|---|---|---|
| HC Group-Type | Blending Stock/Pure Component | Volume Percent |
| Saturates | — | 70.0 |
|  | hydrocracked n-C16 (C6–C16 isomers) | 25.0 |
|  | cyclohexane | 5.0 |
|  | "isopar C" (Exxon isoparaffinic solvent, b.p. = 98–106 deg C.) | 10.0 |
|  | "isopar E" (Exxon isoparaffinic solvent, b.p. = 116–133 deg C.) | 10.0 |
|  | "isopar M" (Exxon isoparaffinic solvent. b.p. = 207–254 deg C.) | 10.0 |
|  | "Exxsol D80" (Exxon aliphatic, high naphthenic solvent, b.p . = 202–232 deg C.) | 10.0 |
| Alkyl Benzenes | — | 20.0 |
|  | toluene | 1.0 |
|  | tetralin | 3.0 |
|  | 1-t-butyl-3-ethylbenzene | 2.5 |
|  | 1-t-butyl-4-ethylbenzene | 2.0 |
|  | 1-t-butyl-3,4,5-trimethylbenzene | 1.5 |
|  | n-octylbenzene | 1.0 |
|  | xylene bottoms (C8–C10 benzenes) | 9.0 |
| Alkyl Naphthalenes | — | 5.0 |
|  | 2-Methylnaphthalene | 2.0 |
|  | 1-ethylnaphthalene | 1.0 |
|  | 1,6-dimethylnaphthalene | 1.0 |
|  | 3,3-dimethylbiphenyl | 1.0 |
| Olefins | — | 5.0 |
|  | 2-heptenes (c,t) | 1.0 |
|  | 1-octene | 2.0 |
|  | 3,5,5-trimethyl-1-hexene | 1.0 |
|  | 1-tridecene | 1.0 |

| Analysis of Sample Mixture 9 | | | |
|---|---|---|---|
|  | HPLC | FIA | Known |
| Saturates | 70.9 | 68.3 | 70.0 |
| Olefins | 4.2 | 5.3 | 5.0 |
| Total Arom. | 24.9 | 26.4 | 25.0 |

EXAMPLE XI

| Composition of Sample Mixture 10, "Simulated" Gasoline | | |
|---|---|---|
| HC Group-Type | Blending Stock/Pure Component | Volume Percent |
| Saturates | — | 60.0 |
|  | hydrocracked n-C16 (C6–C16 isomers) | 10.0 |
|  | petroleum ether (b.p. = 37–55 deg C.) | 30.0 |
|  | "isopar C" (Exxon isoparaffinic solvent, b.p. = 98–106 deg C.) | 20.0 |
| Aromatics | — | 30.0 |
|  | toluene | 5.0 |
|  | xylenes (o-, m-, p-) | 5.0 |
|  | xylene bottoms (C8–C10 benzenes) | 20.0 |
| Olefins | — | 10.0 |
|  | composite mixture of C6s–C16s: | |
|  | 2,3-dimethyl-1-butene | |
|  | 3-methyl-2-pentene | |
|  | 2,4-dimethyl-1,3-pentadiene | |
|  | 1-heptene | |

-continued heptene-3
3-methyl-1-hexene
2,4,4-trimethyl-2-pentene
2-ethyl-1-hexene
2-methyl-1-heptene
1-octene
2,5-dimethyl-1,5-hexadiene
nonene-4 (c,t)
3,5,5-trimethyl-1-hexene
1-decene
1-undecene
1-dodecene
1-hexadecene

Analysis of Sample Mixture 10

|  | HPLC | FIA | Known |
|---|---|---|---|
| Saturates | 60.2 | 57.7 | 60.0 |
| Olefins | 9.9 | 8.7 | 10.0 |
| Total Arom. | 29.9 | 33.6 | 30.0 |

EXAMPLE XII

Composition of Sample Mixture 11, High Olefins Mix

| HC Group-Type | Blending Stock/Pure Component | Volume Percent |
|---|---|---|
| Saturates | petroleum ether (b.p. = 37–55 deg C.) | 60.0 |
| Aromatics | xylene bottoms (CB–C10 benzenes) | 10.0 |
| Olefins | — | 30.0 |
|  | composite mixture of C6s–C16s: |  |
|  | 2,3-dimethyl-1-butene |  |
|  | 3-methyl-2-pentene |  |
|  | 2,4-dimethyl-1,3-pentadiene |  |
|  | 1-heptene |  |
|  | heptene-3 |  |
|  | 3-methyl-1-hexene |  |
|  | 2,4,4-trimethyl-2-pentene |  |
|  | 2-ethyl-1-hexene |  |
|  | 2-methyl-1-heptene |  |
|  | 1-octene |  |
|  | 2,5 dimethyl-1,5-hexadiene |  |
|  | nonene-4 (c,t) |  |
|  | 3,5,5-trimethyl-1-hexene |  |
|  | 1-decene |  |
|  | 1-undecene |  |
|  | 1-dodecene |  |
|  | 1-hexadecene |  |

Analysis of Sample Mixture 11

|  | HPLC | FIA | Known |
|---|---|---|---|
| Saturates | 60.7 | 49.0 | 60.0 |
| Olefins | 29.5 | 34.7 | 30.0 |
| Total Arom. | 9.8 | 16.3 | 10.0 |

EXAMPLE XIII

Analyses of several fuels are given below:

| Sample | HC Group Type | HPLC | FIA |
|---|---|---|---|
| ASTM gasoline standard | saturates | 51.4 | 43.9 |
|  | olefins | 9.4 | 7.0 |
|  | aromatics | 39.2 | 49.1 |
| ASTM gasoline I | saturates | 54.8 | 49.2 |
|  | olefins | 5.7 | 5.1 |
|  | aromatics | 39.5 | 45.7 |
| ASTM gasoline II | saturates | 62.9 | 51.7 |
|  | olefins | 13.0 | 13.8 |
|  | aromatics | 24.1 | 34.5 |
| cat-cracked naphtha | saturates | 56.9 | 44.3 |
|  | olefins | 25.2 | 21.2 |
|  | aromatics | 17.9 | 34.5 |
| ASTM jet fuel standard | saturates | 84.2 | 82.4 |
|  | olefins | 0.0 | 1.3 |
|  | aromatics | 15.8 | 18.6 |
| ASTM jet fuel I | saturates | 84.5 | 82.4 |
|  | olefins | 0.7 | 1.1 |
|  | aromatics | 14.8 | 16.5 |
| ASTM jet fuel II | saturates | 78.3 | 75.7 |
|  | olefins | 3.9 | 2.2 |
|  | aromatics | 17.8 | 22.1 |
| high density jet fuel | saturates | 74.6 | 70.6 |
|  | olefins | 0.0 | 1.5 |
|  | aromatics | 25.4 | 27.9 |
| diesel fuel #2 | saturates | 77.7 | 71.0 |
|  | olefins | 2.0 | 0.7 |
|  | aromatics | 20.3 | 28.3 |
| light pyrolysis fuel | saturates | 12.8 | 0.0 |
|  | olefins | 12.0 | 0.0 |
|  | aromatics | 75.2 | 100.0 |
| hydrostabilized fuel | saturates | 13.1 | 0.0 |
|  | olefins | 2.9 | 0.0 |
|  | aromatics | 84.0 | 100.0 |

Various modifications may be made in the present invention without departing from the spirit of the invention or the scope of the appended claims.

We claim:

1. A method of analysis by high performance liquid chromatography of a sample of hydrocarbon compounds contained in solution into the following three components: saturates, olefins, and total aromatics, which comprises the steps of:
   (a) introducing said sample into an olefin-selective column containing silver-modified cation exchange material;
   (b) thereafter introducing into said column an eluent to elute saturates and total aromatics;
   (c) passing the eluate containing saturates and total aromatics from said column into a dielectric constant detector to detect the eluate quantitatively for saturates and total aromatics;
   (d) backflushing said column with an eluent to elute olefins; and
   (e) passing the eluate containing olefins from said column into said detector to detect the eluate quantitatively for olefins.

2. The method of claim 1 wherein said eluent is 2,2-dichloro-1,1,1-trifluoroethane.

* * * * *

UNITED STATES PATENT AND TRADEMARK OFFICE
CERTIFICATE OF CORRECTION

PATENT NO. : 4,826,603

DATED : May 2, 1989

INVENTOR(S) : Paul C. Hayes, Jr. et al

It is certified that error appears in the above-identified patent and that said Letters Patent is hereby corrected as shown below:

```
Col 1, line  8, correct the spelling of "without".
Col 4, line 25, correct the spelling of "second".
Col 4, line 40, correct the spelling of "unconjugated".
Col 5, line 39, "uantitation" should read "Quantitation".
Col 6, line 55, "p-xylene" should read "p-Xylene".
Col 8, line 34, "Aron." should read "Arom." and should
        appear on the same line as "Polynuclear".
Col 9, line 43, "Naphthalenes" should appear on the same
        line as "Alkyl".
Col 9, line 65, "Naphthalenes" should appear on the same
        line as "Alkyl".
Col 10, line 35, "Naphthalenes" should appear on the same
        line as "Alkyl".
Col 11, line 33, "(CB-C10 benzenes)" should read
        "(C8-C10 benzenes)".
```

Signed and Sealed this

Tenth Day of July, 1990

Attest:

HARRY F. MANBECK, JR.

*Attesting Officer*       *Commissioner of Patents and Trademarks*